US005662583A

United States Patent [19]
Khouri

[11] Patent Number: 5,662,583
[45] Date of Patent: Sep. 2, 1997

[54] MECHANICAL SOFT TISSUE ENLARGER

[75] Inventor: Roger K. Khouri, St. Louis, Mo.

[73] Assignee: Khouri Biomedical Research, Inc., St. Louis, Mo.

[21] Appl. No.: 516,598

[22] Filed: Aug. 18, 1995

[51] Int. Cl.$^6$ .................................................. A01F 5/00
[52] U.S. Cl. .............................. 600/38; 601/14; 602/38
[58] Field of Search ........................... 623/7, 15; 601/14;
606/201, 204.35, 132, 213, 215, 217, 214,
1; 602/38, 54, 74; 600/38–39, 41

[56] References Cited

U.S. PATENT DOCUMENTS

| | | | |
|---|---|---|---|
| 532,236 | 1/1895 | Hardesty | 601/14 |
| 936,434 | 10/1909 | Eganhouse . | |
| 1,021,688 | 3/1912 | Jeune . | |
| 1,312,619 | 8/1919 | D'Orsay . | |
| 1,472,234 | 10/1923 | Thomas | 601/14 |
| 2,012,755 | 7/1935 | Demuth | 606/217 |
| 2,616,417 | 11/1952 | Holbrook . | |
| 2,817,333 | 12/1957 | Cole . | |
| 3,382,867 | 5/1968 | Reaves . | |
| 3,631,853 | 1/1972 | Burdette, Jr. . | |
| 3,785,369 | 1/1974 | Tallent . | |
| 4,368,883 | 1/1983 | Tiktin . | |
| 4,633,865 | 1/1987 | Hengstberger et al. | 606/201 |
| 4,706,661 | 11/1987 | Barrett | 606/215 |
| 4,856,498 | 8/1989 | Osbon . | |
| 4,856,499 | 8/1989 | Kelly . | |
| 5,234,401 | 8/1993 | Yamanaka . | |
| 5,344,396 | 9/1994 | Clark, Jr. . | |
| 5,468,220 | 11/1995 | Sucher | 606/201 |
| 5,476,091 | 12/1995 | Johnson | 606/199 |
| 5,476,478 | 12/1995 | Jackson | 606/204.35 |
| 5,533,499 | 7/1996 | Johnson | 606/199 |

FOREIGN PATENT DOCUMENTS

WO91/17727  11/1991  European Pat. Off. .

OTHER PUBLICATIONS

Copy of *Enlargement Book*, ©1990 Topco Books.
Copy of *An Anthology Of Plastic Surgery*, edited by Harry Hayes, Jr., M.D. specifically Section 6 entitled "Quackery and Nostrums", Aspen Publishers, Inc., 1986, pp. 163–175.
Article entitled "The Tension–Stress Effect on the Genesis and Growth of Tissues— Part 1. The Influence of Stability of Fixation and Soft-Tissue Preservation"by Gavriil A. llizarov, AM., M.D., Ph. D., from *Clinical Orthopaedics and Related Research*, from Section III, entitled Basic Science And Pathology, No. 238, Jan. 1989, pp. 249–281.
Article entitled "The 'Niplette': an instrument for the non-surgical correction of inverted nipples" by D.D. McGeorge, from *British Journal Of Plastic Surgery* 1994, pp. 46–49.
Copy of *How To Enlarge Your Penis*, ©1988 House One, expurgated version.
Brochure entitled "Nipple Enlargement System" by Joel Kaplan, Ph.D., 1993.
Article entitled "The llizarov Technique: A Method To Regenerate Bone And Soft Tissue" by Dror Paley, M.D., et al., pp. 1–41.
Article entitled "The Callotasis Method of Limb Lengthening"by Roberto Aldegheri, M.D., et al., from *Clinical Orthopaedics and Related Research*, No. 241, Apr. 1989, pp. 137–145.
Article entitled "The Expansion Of An Area Of Skin By Progressive Distention Of A Subcutaneous Balloon—Use of the Method for Securing Skin for Subtotal Reconstruction of the Ear", by Charles G. Neumann M.D., from *Plastic And Reconstructive Surgery* Feb., 1957, pp. 124–130.

(List continued on next page.)

*Primary Examiner*—John G. Weiss
*Assistant Examiner*—Bruce E. Snow
*Attorney, Agent, or Firm*—Howell & Haferkamp, L.C.

[57] ABSTRACT

An apparatus for enlarging a patient's soft tissue. The apparatus comprises an adhesive for adhering to said soft tissue and a tensioner connected to the adhesive for applying a tensile stress to the surface of the soft tissue.

18 Claims, 3 Drawing Sheets

OTHER PUBLICATIONS

Article entitled "Tissue Expansion in Soft–Tissue Reconstruction" by Chedomir Radovan, M.D., from *Plastic and Reconstructive Surgery*, Oct. 1984, pp. 482–492.

Artickle entitled "Elongation of Peripheral Nerve and Viscera Containing Smooth Muscle" by Ernest K. Manders, M.D., et al., from *Clinics in Plastics Surgery*, vol. 14, No. 3, Jul. 1987, pp. 551–562.

Article entitled "Rapid Elongation of Arteries and Veins in Rats with a Tissue Expander" by G. Björn Stark, M.D., et al., from *Plastic And Reconstructive Surgery*, Oct. 1987, pp. 570–581.

Article entitled "Histophathology of Human Expanded Tissue" by Krystyna A. Pasyk, M.D., et al., from *Clinics in Plastic Surgery*, vol. 14, No. 3, Jul. 1987, pp. 435–445.

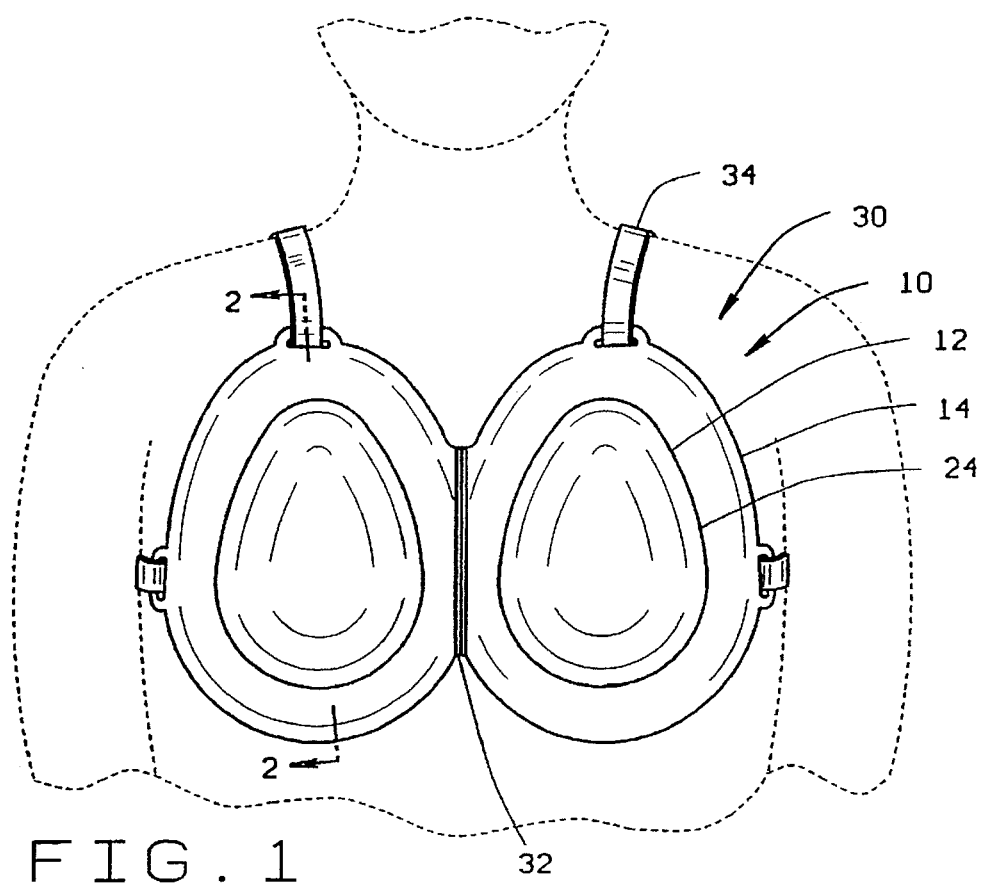
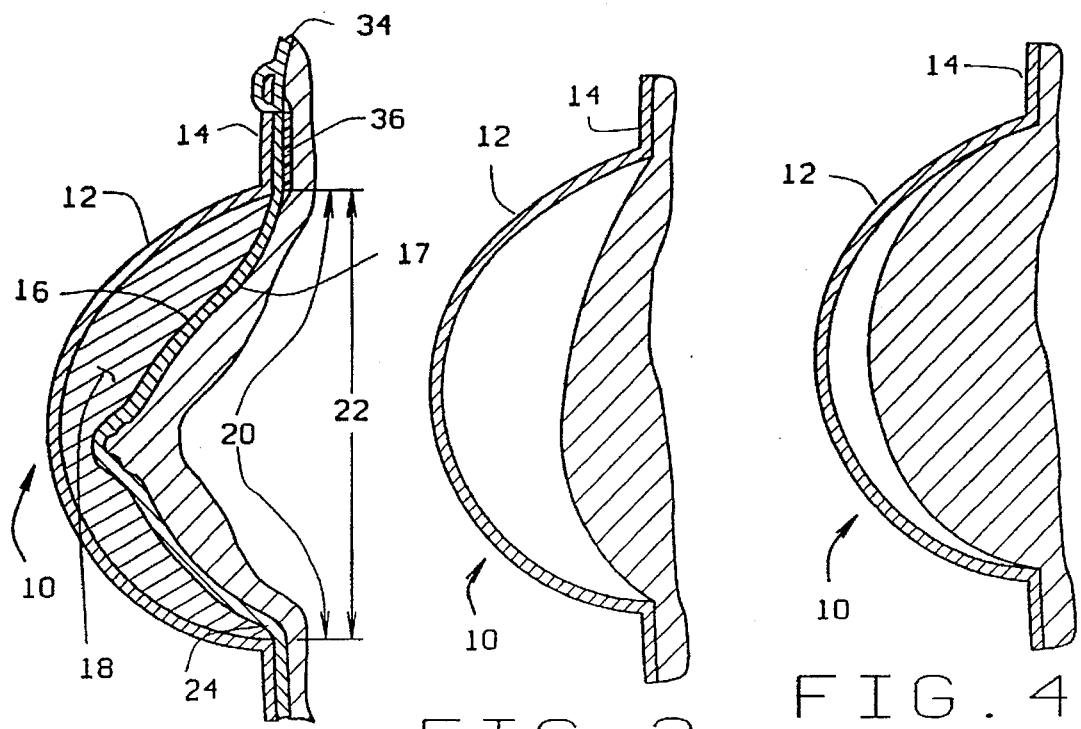

MECHANICAL SOFT TISSUE ENLARGER

BACKGROUND AND SUMMARY OF THE INVENTION

There are numerous instances where persons desire enlargement of the soft tissues in their bodies. One such instance is for the replacement of one or both breasts amputated during a mastectomy in order to restore physiological symmetry and psychological well-being. Other instances are for correction of natural abnormalities such as dimpling. Still other instances are for augmentation of physical attributes to improve cosmetics and self-esteem. These latter soft tissue enlargements are principally directed to breast enlargement in females and penis enlargement in males.

Prosthetic implants have been developed for insertion below the skin. However, the severity of the potential complications including scarring, implant rupture, capsular contracture, necrosis and implant migration as well as the recent adverse publicity thereof have significantly reduced the desirability of these implants. Thus, there is a societal need for other means to obtain soft tissue enlargement.

Some soft tissue enlargements occur naturally. For instance, during pregnancy, the skin over a woman's abdominal region enlarges approximately nine times its previous area to accommodate the fetus without a proportional decrease in skin thickness. In other words, the abdominal skin tissue actually enlarges and does not merely stretch during pregnancy. Similarly, the skin will expand to accommodate any growth under the skin.

In the past, plastic surgeons have used this phenomena to their advantage to expand skin in order to accommodate prosthetic implants. To conduct this procedure, the surgeon inserts a balloon beneath the skin in the area where additional skin is desired. By progressively expanding the balloon, the skin first stretches and eventually actually grows to accommodate the increased volume underneath it. When the desired amount of skin is formed, the balloon is deflated and removed, and the implant is inserted into the cavity left by the balloon. Similar methods have been used by native African tribes to enlarge lips, nostrils, and earlobes.

Other surgical techniques have used tissue expansion to achieve other types of soft tissue growth. For instance, balloons have been successfully expanded underneath nerves, veins, tendons, and the like to thereby elongate these tissues to repair damage and alleviate various abnormalities.

A more advanced surgical method is known as callotasis or limb lengthening. This method comprises cutting the bone about its periphery at the location where lengthening is desired, leaving the tissues inside and around the bone intact. Brackets are attached to the bone on each side of the separation, and the bone segments are slowly pulled away from one another while remaining integral over a period of several months. Not only does this cause the mended bone to be longer, but also the soft tissue surrounding the bone actually grows to accommodate the increased limb length. Similar methods have been used by African native tribes to lengthen necks for cosmetic purposes.

Each of these above-mentioned apparatuses and methods requires an invasive surgical technique to accomplish the soft tissue expansion. Invasive techniques increase the likelihood of the complications associated with the procedure including those mentioned above with respect to implant surgery. In addition, the expense of surgery precludes many persons having their abnormalities corrected or physical attributes enhanced.

Other soft tissue enlargement techniques have been developed which use other mechanisms to cause the enlargement. For instance, an instrument and technique have been developed for the non-surgical correction of inverted nipples due to short lactiferous ducts. The instrument is comprised of a cup having an internal volume shaped like that of the final desired nipple. The user places the cup over the inverted nipple, pumps the air out of the cup with a syringe and adjusts the vacuum within the cup using a check valve to just below the threshold of discomfort. Thus attached, the device puts the lactiferous ducts in tension and extends them sufficiently after two to three months of wear at 8–12 hours per day.

Although this device is sufficient for its intended purpose, it is not suitable for general soft tissue enlargement. Laceration and contusion can occur if too strong of a suction is applied to soft tissue. As the pressure within the inverted nipple instrument is not regulated, contusion or laceration can occur. When a vacuum is developed within the cup of the instrument, an equal and opposite force is applied to the patient about the rim of the cup. Excessive contact forces against the patient can cause ulceration, laceration, and contusions. As the contact forces are not regulated in the nipple instrument, these further complications also can occur. In addition, general soft tissue enlargement is not feasible with the instrument due to the size and shape of the cup.

Another prior art device is disclosed in U.S. Pat. No. 936,434 as a device for enlarging a woman's breasts. This device included a pair of cups for placement on the breasts and a pump for exhausting the air from between the cups and breasts. However, this patent provides no teaching as to the pressures to be used, the potential danger to the skin tissues, or any suggestions as to how the device is to be retained in place during use. Apparently, the device is used in a clinical setting and is not suitable for long term wear such as for 8–10 hours. As the patent suggests that the vacuum acts to cause the veins and arteries to engorge, thereby nourishing the breasts, it is clear that the patentee is suggesting that the breast tissue actually expands through this expansion of blood vessels alone. This patent has been the subject of ridicule by at least one medical authority. See "An Anthology of Plastic Surgery" edited by Harry Hayes, Jr., M.D., Section 6, "Quackery and Nostrums" pub. 1986 by Aspen Publishers, Rockville, Md.

Finally, another prior art device although notorious is worthy of note. This device is commonly referred to as a penis pump and is sold primarily as a novelty as its long-term enlargement efficacy has never been proven and is in fact universally disclaimed by its distributors. The device is comprised of a cylinder having one open end into which the penis is inserted and a pump attached to it such that a vacuum can be created within the cylinder. Not only does this device have the same drawbacks as the nipple instrument with respect to potential complications, but also it is unlikely that sufficient vacuum can be maintained by the device to cause any notable long-term soft tissue enlargement. Further, this device is apparently designed to accomplish two tasks unrelated to enlargement. First, the device is used for stimulation and sexual gratification. Second, the device is used to promote erection by drawing blood into the penis.

Most of these prior art devices and methods have failed to achieve long term soft tissue enlargement while preventing damage to the soft tissue being enlarged, as well as surrounding tissue. The inventor herein has succeeded in designing and developing a new generalized method and apparatus for soft tissue enlargement which prevents damage to soft tissue. The apparatus used for this enlargement is comprised of a variable volume dome which may be adhesively bonded to the skin adjacent the soft tissue and having a rim about its periphery. The rim has sufficient surface area such that the compressive stress applied to the patient by the rim and the tensile stress applied to the soft tissue under the dome are both applied at levels and for periods of time below which damage will not occur to the underlying soft tissue. In addition, a stress sensing device may be incorporated into the enlargement apparatus to assure that the compressive and tensile stresses are below predetermined limits where tissue damage would occur. As the previously mentioned pressure limits are ready converted to common units of stress or units of force, these limits may alternately be set in stress or force units.

In implementing the device of the present invention, the inventor intends that it be capable of achieving its therapeutic effect without creating any long term tissue necrosis from use. In other words, a tensile stress must be applied to the desired area to achieve the therapeutic effect for sufficient periods of time without applying too great a tensile or compressive stress which will damage the underlying tissue. As considered from this generalized approach, one of ordinary skill in the art would understand the inventor's teaching to include the idea of providing a smaller tensile stress caused by the enlarger and balancing that tensile stress with a rim having a surface area less than the normal area of the dome, thereby creating a greater compressive stress which is still within acceptable limits. Still another approach which may very well provide a therapeutic effect would be to cycle the tensile stress such that it is applied for periods of time at elevated levels and relaxed levels so that the rim might also have a cross-sectional area less than the normal area of the dome, but yet avoid creating any tissue necrosis. Therefore, the invention should be understood as being limited only by the current medical understanding of the causative effects of pressure sores and other tissue damage by an applied tensile or compressive stress.

It is well recognized in the medical literature that decubitus ulcers are caused by unrelieved external pressure or compressive stress that occludes blood flow and results in tissue necrosis. In recognition of this fact, these ulcers are called pressure sores. The average capillary pressure in human skin is around 15–20 mmHg. E. M. Landis, *Micro-Injection Studies of Capillary Blood Pressure in Human Skin*, 15 Heart 209–228, (1930). For convenience, 20 mmHg will be used to describe this pressure throughout the remainder of this description. However, it should be understood that pressures below 20 mmHg may also be used without departing from the scope of this invention and that these lower pressures may provide additional margins in preventing damage to tissues. Likewise, when an equivalent stress value is used, the equivalent range in stresses is also intended. Therefore, the local application of an external pressure up to 20 mmHg will not collapse capillaries adjacent the location of the applied pressure and thus will not disturb the circulation. Therefore, local application of contact pressures less than or equal to 20 mmHg are well tolerated for prolonged periods of time. This tolerance has been confirmed by the inventor through use of a prototype which did not cause adverse effects after many hours of continuous use as long as the pressure under the rim remained below or around 20 mmHg.

Pressures greater than 20 mmHg will occlude the capillaries and stop tissue perfusion. Tissues can tolerate short periods of ischemia, but if the pressure is continuous and perfusion is not restored within a relatively short period of time, tissue damage will ensue. "The time factor is thus more important than pressure intensity". A pressure of 100 mmHg will lead to pathologic changes after only two hours. T. Hussain, *An Experimental Study of Some Pressure Effects on Tissues, with Reference to the Bed-Sore Problem*, 66 J. Path. Bact. 347–358, (1953).

The experimental results of additional investigators can be used to develop a safe time-pressure curve above which tissue damage will ensue. For instance, 20 mmHg is well tolerated for prolonged periods of time, but 40 mmHg will lead to tissue injury if the pressure is not relieved for 13 hours. The injury is more severe if the pressure is 60 mmHg, and even greater injury will result with a pressure of 100 mmHg after shorter periods of time. O. Lindan, *Etiology of Decubitus Ulcers: An Experimental Study*, 42 Arch. Phys. Med. Rehab. 774–783, (1961). Similarly, a pressure of 70 mmHg, if unrelieved, will lead to pathologic changes after 2 hours. However, if the pressure is intermittent, applied 5 minutes on, and 5 minutes off, there is no pathologic tissue changes. M. Kosiak, *Etiology of Decubitus Ulcers*, 42 Arch. Phys. Med. Rehab. 19–29, (1961).

These findings are consistent with the clinical testing of the prototype of the breast device. It was found that a continuous pressure under the rim of 40 mmHg could be tolerated for only one hour by healthy volunteers. After one hour, the volunteers started to complain of pain which is the warning sign of impending tissue damage. Higher pressures led to pain under the rim after even shorter periods of tame. Lower pressures around 30 mmHg led to pain after 4 hours. However, if the pressure is allowed to cycle, that is if it is dropped down to 0–20 mmHg to allow the tissues to temporarily reperfuse for a few minutes, higher peak pressures can be tolerated. The higher the peak pressures, the shorter they are tolerated and the longer the low pressure part of the cycle needs to be to allow the tissues to recuperate. As will be readily appreciated by those of ordinary skill in the art, these pressure limits are easily converted to units of stress. Thus, rather than pressure limits, stress limits may be set. Likewise, as the relevant areas of interest may also be known, these stress limits may easily be converted to force limits by multiplying the particular stress limit by the appropriate known area measurement. Thus, limits may be set using any one of several measurement units depending upon scale desired.

Therefore, pressures under the rim greater than 20 mmHg can only be tolerated if there is a means to continuously cycle the pressure peaks on and off allowing for tissue re-perfusion during the off periods. The higher the peaks, the shorter the pressures are tolerated and the longer the period of low pressure recuperation needs to be.

From the above experimental animal data and human study, the inventor concludes that 20 mmHg is the highest pressure that can be safely tolerated under the rim on a prolonged basis. Higher pressures can only be applied intermittently, and then cycled down to less than 20 mmHg. As a pressure of 20 mmHg is equivalent to a stress of approximately $2666 N/m^2$, the rim stress may be limited alternatively to this stress level instead.

The method of use is comprised of the steps of attaching the variable volume dome to the location of desired enlargement, and expanding the dome. In the continuous application method in which the stress is applied at levels that can be withstood continuously, the stress should be maintained for a minimum of eight hours per day and results should be sufficient after several months.

As indicated by the summary of the medical literature given above, the present invention may also be used in alternative methods in keeping within the scope of the inventor's concept. For example, the device might have a rim cross-sectional area substantially less than the normal area of the dome and be used in either of two methods. In a first method, a somewhat lower tensile stress may be induced in the dome such that the opposing compressive stress under the rim may be maintained at bearable levels for extended periods of time and yet provide a therapeutic effect. Alternatively, the vacuum tensile stress may be regulated in a routine which provides somewhat higher stresses for shortened periods of time separated by periods of lower stress to allow tissue reperfusion. In other words, alternating cycles of high stress, tissue reperfusion, high stress, tissue reperfusion, etc., may achieve a therapeutic effect in enlarging the soft tissues. With either of these methods, the rim may have a cross-sectional area substantially less than the normal area of the dome.

In implementing the present invention, the inventor has found that it is desirable to provide a gasket around the rim of the dome which has the ability to distribute the shearing forces generated between the skin and rim as the tensile stress is applied. In one embodiment, this is achieved by providing a rim made of silicone gel which has a thickness sufficient to allow its surface adjacent the skin to shift laterally with respect to the dome. In this way, the shearing stress is distributed along virtually the entirety of its contact surface and even beyond the periphery of the rim. Thus, the shearing stress is not concentrated as a high contact stress at the edge of the rim adjacent the pressurized area under the dome. As an alternative to a gel-like rim, the inventor has also considered the use of a balloon-like or inflated rim as specific embodiments of this aspect of the invention. Other configurations and constructions would be suitable, it only being desired to provide for a relative lateral shift between the dome and the surface of the rim which contacts the soft tissue as the tensile stress is applied to thereby distribute the shearing stress across the surface of the rim and beyond.

While the practical advantages and features of the present invention and method have been briefly described above, a greater understanding of the novel and unique features of the invention may be obtained by referring to the drawings and Detailed Description of the Preferred Embodiment which follow.

BRIEF DESCRIPTION OF THE DRAWINGS

FIG. 1 is a front elevation view of the soft tissue enlargement apparatus of the present invention, showing the breast augmentation embodiment;

FIG. 2 is a cross-sectional view of the breast enlargement embodiment taken in the plane of line 2—2 of FIG. 1;

FIG. 3 is a cross-sectional schematic of a dome and soft tissue in the early stages of enlargement;

FIG. 4 is a cross-sectional schematic of a dome and soft tissue in the latter stages of enlargement;

DETAILED DESCRIPTION OF THE PREFERRED EMBODIMENT

Figure 5:
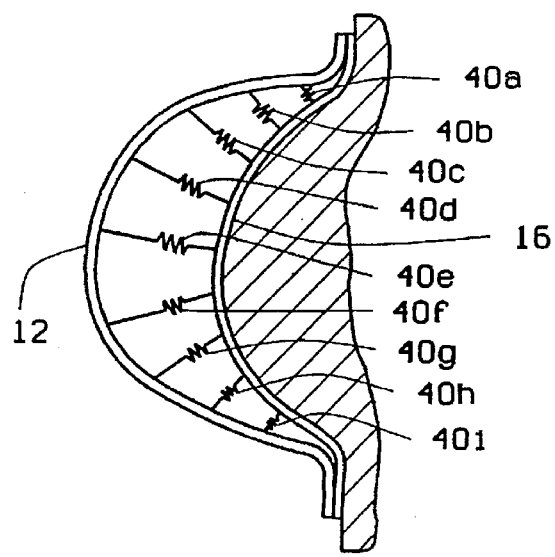
FIG. 5 is a cross-sectional schematic of an alternate embodiment wherein the intermediate material is replaced with a plurality of elastic filaments.

As shown in FIGS. 1 and 2, one embodiment of the soft tissue enlargement apparatus 10 of the present invention is generally comprised of a dome 12 having a rim 14, a flexible sheet 16, and an intermediate material 18 sandwiched between the dome and flexible sheet. The material 18 may be any compliant material which when cured shrinks to a smaller volume. Depending upon the material chosen, the curing may be accelerated by ultraviolet light or other known means. The sheet 16 is adhesively bonded to the soft tissue underlying the dome using double-sided tape, sheets or other detachable adhesive means 17. The adhesive means 17 may comprise typical adhesives or glues, as well as, sticky gels or sheets of double-sided adhesive tapes. Further, the adhesive means 17 may be an adhesive substance embedded in the sheet 16 or rim 14. As the material 18 shrinks upon curing, the sheet 16 and therefore the soft tissue which is bonded to it are drawn toward the rigid dome 12. In doing so, tensile stresses are developed in the soft tissue which over time cause the tissue to enlarge. The removeable adhesive means 17 makes attachment more convenient as the adhesive means may be removed from the flexible sheet 16 when it has lost the ability to adhere to the skin. A new adhesive means 17 may be applied to the sheet 16 before the next application of the apparatus 10 to assure that slippage does not occur.

Several forces are developed within the dome and about the rim as a result of the stresses induced by the shrinking material. A tensile force $F_t$ is developed within the material equal to the tensile stress $S_1$ in the soft tissue multiplied by the enclosed soft tissue surface area $A_s$ 20. The vector sum of the tensile force is referred to as the normal force $F_1$ and is equal to the tensile stress $S_1$ developed in the soft tissue multiplied by the normal area $A_1$ 22 of the dome opening, i.e., $F_1=S_1A_1$. The normal area $A_1$ is the projected area bounded by the periphery 24. An opposing force $F_2$ is imposed upon the user by the rim 14 to balance the normal force $F_1$ and is equal to, but opposite, the normal force. This opposing force $F_2$ develops a compressive stress $S_2$ in the soft tissue underlying the rim 14. The compressive stress $S_2$ under the rim 14 is equal to the opposing force $F_2$ divided by the rim surface area $A_2$ 26, i.e., $S_2=F_2/A_2$ or $F_2=S_2A_2$. As the magnitude of the opposing force is equal to the magnitude of the normal force, $F_1=F_2$ and $S_1A_1=S_2A_2$. Therefore, if the rim surface area $A_2$ 26 is configured to be equal to the normal area $A_1$ 22 at the dome opening, then the compressive stress in the patient's underlying tissue will not exceed the magnitude of the vacuum within the dome 12, i.e., $S_2=S_1$. Thus, the rim surface area $A_2$ 24 may be sized with respect to the normal area $A_1$ 22 so that the compressive stress $S_2$ is maintained below $2666N/m^2$ when the tensile stress $S_1$ within the soft tissue is maintained at less than $2666N/m^2$. As studies have shown that no damage occurs to typical soft tissue in humans at tensile or compressive stresses below $2666N/m^2$, even when the stresses are applied over an extended period of time, this limit should not be exceeded when relatively long periods of use at constant stresses are desired. However, if the tensile stress is cycled, different area ratios may be used to optimize the therapeutic effects while minimizing the potential for damage to the soft tissue within the dome or beneath the rim.

In the specific embodiment shown in FIGS. 1 and 2, the rim 14 has a surface area 28 equal to the normal area 32 of the dome opening thereby preventing medical complications to the soft tissue beneath the rim as long as the tensile stress is properly regulated within the dome 12. However, alternate embodiments having a rim 14 with a surface area 26 equal to or less than the normal area 22 of the dome opening may be used depending upon the amplitude of the tensile stress used and depending upon whether the tensile stress is constant or varied.

As shown in FIG. 1, one specific embodiment may take the form of a bra 30 having two domes 12 spaced by a hinge 32. Straps 34 may be attached to the bra 30 to retain the bra 30 in place. A gasket 36 may also be included about the rim 14 to improve the patient's comfort and reduce shear stresses in the soft tissue as will be explain in greater detail below. In the preferred embodiment, this gasket 36 may be a silicone gel cushion or other soft, conforming material having a sufficient thickness to permit the skin under the rim to shift laterally when excessive shear forces are imposed.

In another general embodiment, the tensile stress $S_1$ may be applied using elastic filaments or springs instead of the intermediate material to develop the tensile stress in the soft tissue. One such alternate embodiment is shown schematically in FIG. 5. In this embodiment, a flexible sheet of material 16 may be adhesively bonded to the soft tissue which is desired to be enlarged. A plurality of elastic filaments 40a–i may be connected at spaced intervals to the sheet of material 16. These filaments 40a–i may also be connected to the inner surface of the dome 12 so that they are held in tension and the desired tensile force $F_t$ is applied to the sheet and thus the desired tensile stress $S_1$ is induced in the soft tissue enclosed by the dome. Depending upon the filament spacing and the pre-set tension, the tensile force $F_t$ may be varied from place to place within the dome 12.

Figure 6:
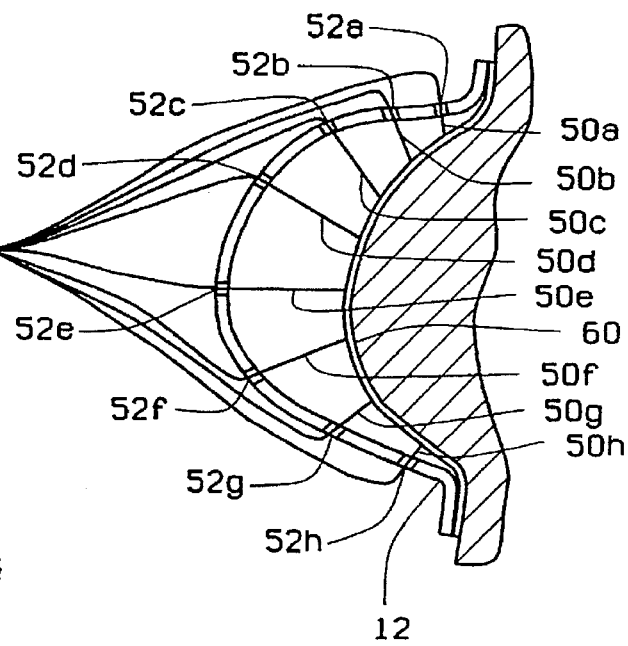
FIG. 6 is a cross-sectional schematic of a second alternate embodiment which is similar to that of FIG. 5 except that the filaments are substantially non-extensible.

A variant embodiment using the same principal is shown in FIG. 6. In this variant embodiment, the sheet of material 60 is again applied to the desired soft tissue with an adhesive. However, in place of the filaments 40a–i, non-extensible filaments 50a–h made of a suitable material may be attached to the sheet of material 16 and may be positioned to extend through a plurality of holes 52a–h in the dome 12. These filaments 50a–h may be joined or individually tensioned using springs, weights, or any other known means to subject the soft tissue to the tensile stress $F_t$. As with the alternate embodiment shown in FIG. 5, the variant embodiment shown in FIG. 6 may have a tensile force $F_t$ which varies from place to place by varying the spacing and tensioning of the filaments 50a–h.

Imposing a constant tensile force $F_t$ in the filaments such as by using a weight attached to the embodiment shown in FIG. 6 has an advantage over using a tensioning means which relaxes as the soft tissue enlarges. If the tissue only slightly protrudes into the dome as shown in FIG. 3 and as is typically the initial condition, then the surface area 20 under the dome is only slightly larger than the normal area 22 at the dome opening. Therefore, the tensile stress $S_1$ acts on a surface area 20 which approaches the minimal value of the normal area. As enlargement occurs, more tissue protrudes into the dome 12 as shown in FIG. 4 thereby providing more surface area 20 under the dome. Because the surface area 20 under the dome is larger, the area over which the tensile stress acts is larger. For a given stress level, the enlargement of the soft tissue is a function of the surface area. Therefore, the total rate of enlargement of the soft tissue increases as treatment continues because the surface area under the dome is ever increasing. This however has no effect on the opposing force, or for that matter the normal force, as the tensile force $F_t$ is a vector which must always sum into the normal force. In other words, a unit of surface area enlarges at a constant rate for any given stress, but as the soft tissue surface area under the dome increases, there are more units of surface area increasing at the constant rate. Therefore, the total rate of enlargement increases as treatment continues even though the tensile stress is not increased.

Figure 7:
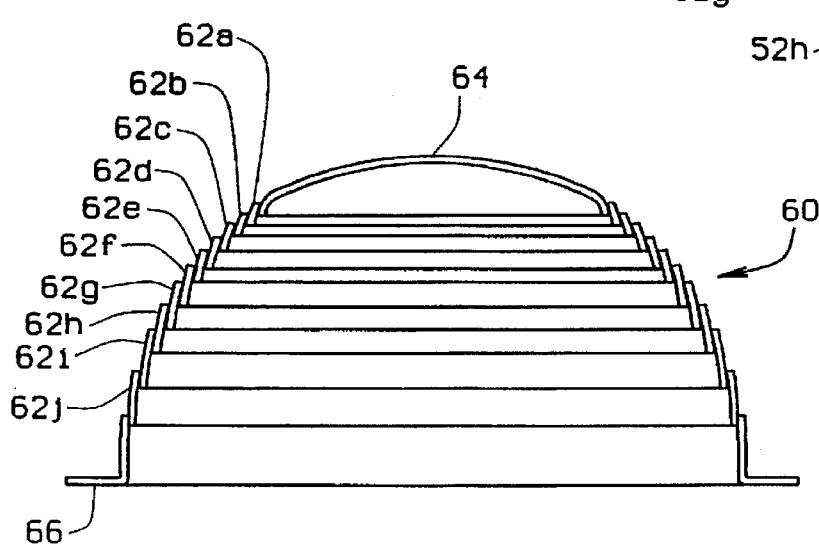
FIG. 7 is a cross-sectional view of a collapsible dome used in a third alternate embodiment.

Still another alternate embodiment is shown in FIG. 7. In this embodiment, the soft tissue may be directly bonded to a collapsible dome 60. The dome is comprised of a plurality of concentric annular bands 62a–j an end plate 64, and an annular rim flange 66. By collapsing and/or extending the collapsible dome, stress may be induced or relieved in the soft tissue. Alternately, this alternate embodiment shown in FIG. 7 may be used with a flexible sheet 16 and a compliant intermediate material or spaced filaments as explained above. Various locking means may be used with this embodiment to hold the dome 60 in differing states of extension to induce differing states of stress in the soft tissue. Likewise, the annular bands 62a–j may be formed with helical interlocking interfaces so that the dome is expandable by rotation rather than axial displacement.

Figure 8:
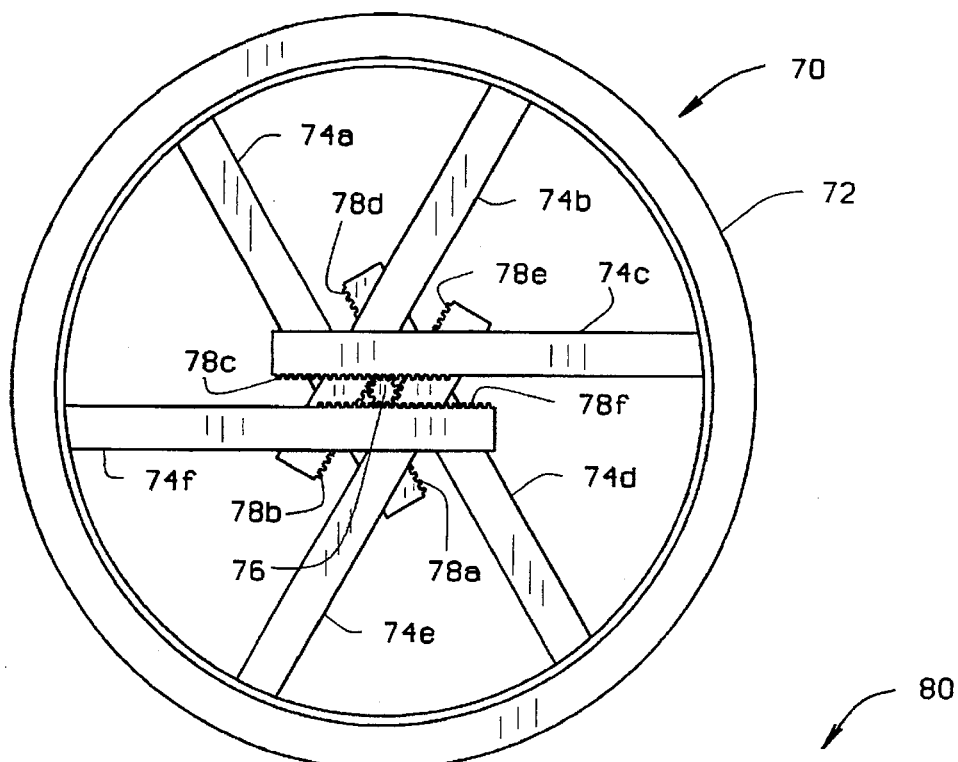
FIG. 8 is a rear elevation view of a collapsible frame used in a fourth alternate embodiment.
Figure 9:
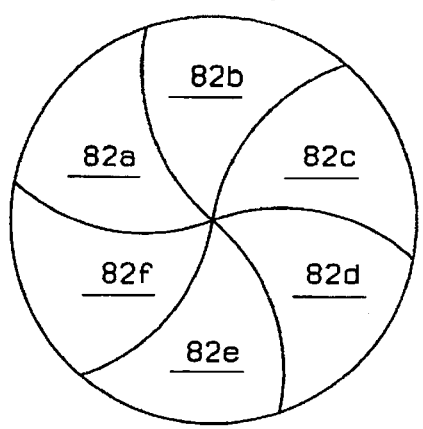
FIG. 9 is a rear elevation view of a collapsible frame used in a fifth alternate embodiment.
Figure 10:
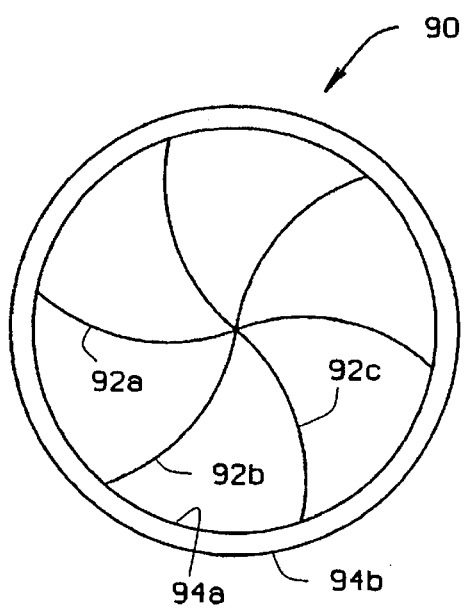
FIG. 10 is a rear elevation view of a collapsible frame used in a sixth alternate embodiment.
Figure 11:
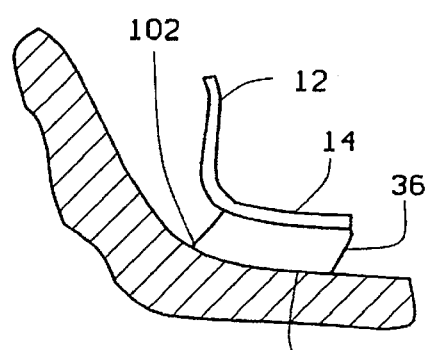
FIG. 11 is a cross-sectional view of an alternate embodiment having a flexible rim gasket for distributing the forces along the time of the frame or dome.

Yet another alternate embodiment is shown in FIG. 8 which employs a variable volume dome or frame 70 rather than a rigid dome 12. The frame 70 is comprised of a rim flange 72 similar to that of the previously described embodiment. Attached to the rim flange 72 are arcuate bands 74a–f which extend upward and inward toward a pinion 76 located generally along the centerline of the rim flange. Each of the arcuate bands 74a–f includes a rack 78a–f which engages the pinion 76. By rotating the pinion 76, the bands 74a–f are forced either outward or inward to change the enclosed volume of the frame 70. Because the frame is attached to the soft tissue, this change in volume induces a change in stress within the soft tissue. As with the previously described embodiment, this frame may be directly applied to the soft tissue or attached to a sheet 16 which is adhesively bonded to the soft tissue. By turning the pinion, the tensile stress in the soft tissue may be adjusted. Variations of this embodiment may have more or fewer than the six arcuate bands 72a–f shown. FIG. 9 shows a variation of the FIG. 8 embodiment where an iris mechanism 80 made from leaves 82a–f is substituted for the arcuate band with rack and pinion system shown in FIG. 8. FIG. 10 shows a variation of the FIG. 9 embodiment where a frame 90 made from a plurality of arcuate bands 92a–c are attached to two concentric annular rim flanges 94a,b. Rotation of the rim flanges 94a,b displaces the ends of the arcuate bands 92a–c and thereby flexes the bands out of plane to enlarge or reduce the volume enclosed by the resulting frame 90. As with the embodiment of FIG. 8, the embodiments of FIGS. 9 and 10 may also have fewer or more leaves and bands.

In each of the above-described embodiments, the gasket 36 attached to the rim 14 may be configured to distribute any shear forces generated between the skin and rim as the tensile force is applied. This shear force distribution may be accomplished with the use of a silicone gel or inflated membrane or bladder which has a thickness sufficient to allow its surface 100 adjacent the soft tissue to shift laterally with respect to the rim. In this way, the shearing force is distributed along the surface 100 adjacent the soft tissue so that the force is not concentrated at the edge 102 of the rim adjacent the dome. In addition to distributing the shear forces over a larger area, the gel or other flexible rim material provides a cushion to improve the user's comfort and inhibit contusions should an unintentional impact be applied to the dome.

In order to use the invention, the patient places the dome over the area of desired enlargement and adjusts the straps for comfort. Then the patient simply actuates the tensile force generating means and the device goes to work. These apparatuses are intended to be worn 8-12 hours per day and can be worn during sleep. After several months, notable and long-term enlargement should occur. When the desired enlargement is achieved, the use of the device may be suspended. If additional enlargement is desired, then use may be continued. Occasional use or use at a reduced pressure may also be desired to maintain the desired enlargement.

There are various changes and modifications which may be made to the invention as would be apparent to those skilled in the art. However, these changes or modifications are included in the teaching of the disclosure and it is intended that the invention be limited only by the scope of the claims appended hereto.

What is claimed is:

1. An appliance for enlarging a patient's soft tissue, said appliance comprising:

an adhesive for adhering to a surface of said soft tissue;

a tensioner connected to said adhesive for applying a normal tensile force to the adhesive to thereby develop a normal tensile stress in said soft tissue; and a support attached to said tensioner, said support having a surface area configured for engaging said patient about a periphery of the surface of said soft tissue for counterbalancing said tensile force with a compressive force against said patient.

2. The appliance of claim 1 wherein said tensioner and support are configured to apply the tensile force and the counterbalancing compressive force at values and for periods of time which will not cause damage to any underlying tissue.

3. The appliance of claim 2 wherein said counterbalancing compressive force is distributed over the surface area of said support, and said tensioner includes a normal area generally defined by said surface area and over which said tensile force is applied, said normal area being smaller than or equal to said surface area.

4. The appliance of claim 1 wherein said tensioner is configured to apply a substantially uniform tensile stress across the surface of the soft tissue.

5. The appliance of claim 4 wherein said tensioner includes a frame overlying said adhesive and a volume of material which shrinks upon curing positioned between the frame and the adhesive.

6. The appliance of claim 4 wherein said tensioner is configured to apply the substantially uniform tensile stress across the surface of the soft tissue at any of several different levels.

7. The appliance of claim 6 wherein said tensioner is manually adjustable.

8. The appliance of claim 7 wherein said tensioner includes an iris apparatus for varying the tensile stress on the surface of the soft tissue.

9. The appliance of claim 7 wherein said tensioner includes a plurality of generally arcuate bands configured to enclose a volume, said bands being configured to actuate to vary the volume enclosed.

10. The appliance of claim 7 wherein said tensioner includes a frame overlying said adhesive and a plurality of filaments extending between the frame and the adhesive, the filaments being in a state of tension.

11. The appliance of claim 10 wherein each of said filaments is substantially non-extensible.

12. The appliance of claim 10 wherein each of said filaments is elastic.

13. The appliance of claim 1 wherein said adhesive includes a replaceable double-sided adhesive sheet.

14. The appliance of claim 1 wherein said adhesive includes a sticky gel.

15. The appliance of claim 1 wherein said adhesive includes a glue.

16. The appliance of claim 1 further comprising a sheet to which said adhesive is applied for adhering the appliance to the soft tissue.

17. The appliance of claim 16 wherein said adhesive is embedded in said sheet.

18. The appliance of claim 1 further comprising an inner liner positioned between said adhesive and said tensioner, said liner having sufficient compliance and resilience to conform to the soft tissue.

* * * * *